United States Patent
Heidemann et al.

(10) Patent No.: US 8,962,508 B2
(45) Date of Patent: Feb. 24, 2015

(54) PROCESS FOR TREATING SHAPED CATALYST BODIES AND SHAPED CATALYST BODIES HAVING INCREASED MECHANICAL STRENGTH

(71) Applicant: BASF SE, Ludwigshafen (DE)

(72) Inventors: Thomas Heidemann, Viernheim (DE); Claudia Özkozanoglu, Kaiserslautern (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/972,401

(22) Filed: Aug. 21, 2013

(65) Prior Publication Data
US 2014/0058134 A1    Feb. 27, 2014

Related U.S. Application Data

(60) Provisional application No. 61/691,829, filed on Aug. 22, 2012.

(51) Int. Cl.
| | | |
|---|---|---|
| *B01J 29/70* | (2006.01) | |
| *B01J 23/72* | (2006.01) | |
| *B01J 21/06* | (2006.01) | |
| *B01J 23/75* | (2006.01) | |
| *B01J 23/755* | (2006.01) | |
| *C07C 209/60* | (2006.01) | |
| *B01J 37/06* | (2006.01) | |
| *B01J 37/08* | (2006.01) | |
| *B01J 35/00* | (2006.01) | |
| *B01J 37/02* | (2006.01) | |

(52) U.S. Cl.
CPC .............. *B01J 29/7007* (2013.01); *B01J 23/75* (2013.01); *B01J 23/755* (2013.01); *B01J 23/72* (2013.01); *B01J 21/063* (2013.01); *C07C 209/60* (2013.01); *B01J 37/06* (2013.01); *B01J 37/08* (2013.01); *B01J 35/002* (2013.01); *B01J 37/0201* (2013.01); *Y10S 502/503* (2013.01); *Y10S 502/514* (2013.01); *Y10S 502/523* (2013.01)
USPC .............. 502/60; 502/260; 502/331; 502/346; 502/350; 502/503; 502/514; 502/523; 564/485

(58) Field of Classification Search
USPC .......................................... 502/503, 514, 523
See application file for complete search history.

(56) References Cited

U.S. PATENT DOCUMENTS

| | | | | |
|---|---|---|---|---|
| 5,217,940 | A | * | 6/1993 | Halabi et al. ................... 502/355 |
| 6,049,008 | A | * | 4/2000 | Roberts et al. ................ 564/422 |
| 6,291,715 | B1 | | 9/2001 | Ruider et al. |
| 7,135,531 | B2 | * | 11/2006 | Zhu et al. .................... 526/124.3 |
| 2004/0220428 | A1 | | 11/2004 | Gerlach et al. |
| 2006/0116517 | A1 | | 6/2006 | Bosch et al. |
| 2009/0093654 | A1 | | 4/2009 | Hahn et al. |
| 2012/0041236 | A1 | | 2/2012 | Heidemann et al. |
| 2012/0071692 | A1 | | 3/2012 | Ahrens et al. |
| 2012/0245389 | A1 | | 9/2012 | Wigbers et al. |
| 2012/0245390 | A1 | | 9/2012 | Wigbers et al. |
| 2012/0289747 | A1 | | 11/2012 | Konigsmann et al. |
| 2013/0131339 | A1 | | 5/2013 | Heidemann et al. |

FOREIGN PATENT DOCUMENTS

| | | |
|---|---|---|
| DE | 19942300 A1 | 3/2001 |
| DE | 103 26 137 A1 | 12/2004 |
| EP | 1431273 A1 | 6/2004 |
| EP | 1996543 A1 | 12/2008 |
| WO | WO-2004108280 A1 | 12/2004 |
| WO | WO-2010121974 A2 | 10/2010 |
| WO | WO-2011048128 A2 | 4/2011 |

OTHER PUBLICATIONS

De Jong, K.P., "Shaping of Solid Catalysts", Synthesis of Solid Catalysts, Wiley-VCH, (2009), pp. 173-183.

* cited by examiner

*Primary Examiner* — Brian J Davis
(74) *Attorney, Agent, or Firm* — Drinker Biddle & Reath LLP

(57) ABSTRACT

The present invention provides a process for treating shaped catalyst bodies which has the following steps:
  a) providing finished shaped catalyst bodies,
  b) impregnating the finished shaped catalyst bodies with a peptizing auxiliary in an amount of liquid which does not exceed the theoretical water absorption of the shaped catalyst bodies,
  c) thermal treating the impregnated shaped catalyst bodies at from 50° C. to 250° C. and
  d) calcinating the thermally treated shaped catalyst bodies at from 250° C. to 600° C.
  A shaped catalyst body which has increased mechanical strength and can be produced by the process of the invention is also provided. The present invention relates to the use of the shaped catalyst bodies of the invention for preparing amines and also in fixed-bed reactors or fluidized-bed reactors and to a chemical synthesis process in the presence of shaped catalyst bodies according to the present invention.

20 Claims, No Drawings

PROCESS FOR TREATING SHAPED CATALYST BODIES AND SHAPED CATALYST BODIES HAVING INCREASED MECHANICAL STRENGTH

This patent application claims the benefit of pending U.S. provisional patent application Ser. No. 61/691,829 filed on Aug. 22, 2012, incorporated in its entirety herein by reference.

The present invention relates to a process for treating shaped catalyst bodies, in particular increasing the mechanical strength thereof, in which finished shaped catalyst bodies are impregnated with peptizing auxiliaries and subsequently thermally treated. The invention further relates to shaped catalyst bodies having increased mechanical strength which can be produced by the process of the invention, and also their use.

Shaped catalyst bodies are used widely. They are generally in the form of pieces, e.g. pellets or extrudates. In order to be able to use such shaped catalyst bodies safely and reliably under industrially relevant conditions, for example also in fixed-bed reactors and in fluid-bed reactors, they have to have a sufficient mechanical strength. Here, it has to be taken into account that the shaped catalyst bodies can also lose mechanical strength over time during use.

According to the prior art, there are many methods of attaining a satisfactory mechanical strength available, which are employed during the respective production processes, so that the setting of the required mechanical strength is generally concluded with the finished production of the conventional shaped catalyst bodies.

Thus, according to the prior art (cf., for example, K. P. de Jong, "Synthesis of Solid Catalysts", Wiley-VCH, 2009, pp. 173-183), for example in the production of extrudates, the starting materials to be extruded are admixed with peptizing auxiliaries before the actual shaping operation, in order to form reactive groups on the surface of the solids used, which groups lead, during the shaping process and in an optional subsequent thermal treatment step, to network formation and thus to hardening of the resulting shaped catalyst bodies. Here, various substances which can be removed without leaving a residue up to the end of the respective production process are used as peptizing auxiliaries, WO 2010/121974 A2 describes, inter alia, hydroamination catalysts based on zeolites, in particular boron-beta-zeolites which are subject to various modifications to increase the selectivity, the operating life and the number of possible regenerations, with these modifications being carried out before the finished production of the respective shaped catalyst bodies, i.e. before the final calcination. For this purpose, for example, acids or acid mixtures are used for treating the shaped or unshaped material.

WO 2004/108280 A1 discloses a process for increasing the cutting hardness of a shaped body, in which a shaped body comprising a crystalline aluminosilicate (zeolite) is treated with a gas comprising water vapor at a temperature of from 100° C. to 600° C. and an absolute pressure of from 0.1 bar to 20 bar for a time of at least 20 hours. The mechanical properties of a shaped body which has been treated in this way can be improved further by at least 20% after calcination.

The methods known in the prior art for providing shaped catalyst bodies with a higher mechanical strength are consequently either restricted to modification of the original production process (cf., for example, K. P. de Jong, "Synthesis of Solid Catalysts", Wiley-VCH, 2009, pp. 173-183) or are very specifically designed for particular catalyst systems (cf. WO 20101121974 A2) or lead to an improvement only with a great additional outlay in terms of apparatus and time (cf. WO 2004/108280 A1).

In view of this background, it is an object of the invention to provide a generally applicable process by means of which the mechanical strength of existing shaped catalyst bodies can be increased further. A further object of the invention is to create shaped catalyst bodies having increased mechanical strength.

This object is achieved, in a first aspect of the present invention, by a process for treating shaped catalyst bodies, which comprises the process steps:
a) provision of finished shaped catalyst bodies,
b) impregnation of the finished shaped catalyst bodies with a peptizing auxiliary in an amount of liquid which does not exceed the theoretical water absorption of the shaped catalyst bodies,
c) thermal treatment of the impregnated shaped catalyst bodies at from 50° C. to 250° C. and
d) calcination of the thermally treated shaped catalyst bodies at from 250° C. to 600° C.

This object is achieved, in a first aspect of the present invention, further by a process for increasing the mechanical strength of shaped catalyst bodies, which comprises the process steps:
a) provision of finished shaped catalyst bodies,
b) impregnation of the finished shaped catalyst bodies with a peptizing auxiliary in an amount of liquid which does not exceed the theoretical water absorption of the shaped catalyst bodies,
c) thermal treatment of the impregnated shaped catalyst bodies at from 50° C. to 250'C and
d) calcination of the thermally treated shaped catalyst bodies at from 250° C. to 600° C.

The present invention is based on the recognition that the mechanical strength of even finished shaped catalyst bodies of widely differing shapes and a variety of compositions can be improved further when these are subjected to the process of the invention. Here, the process of the invention can be applied not only to freshly produced shaped catalyst bodies but also to commercial products and even shaped catalyst bodies which have been previously used and regenerated before the treatment.

Here, the shaped catalyst bodies are impregnated with a peptizing auxiliary, with it being important that impregnation is carried out using only an amount of liquid peptizing auxiliary which does not exceed the theoretical water absorption of the shaped catalyst bodies. This is also referred to as the "incipient wetness" method, i.e. even though the shaped catalyst bodies have absorbed the maximum amount of liquid peptizing auxiliary during the impregnation according to the invention, they continue to appear dry on the outside, i.e. no liquid exits to the outside.

The theoretical water absorption can be determined by determining the open pore volume of the shaped catalyst bodies, which can be measured by known methods such as water absorption or mercury porosimetry. The impregnation itself can be carried out by any method with which those skilled in the art are familiar. For the purposes of the process of the invention, the shaped bodies are preferably initially charged and the liquid is introduced at room temperature with rotary motion of the bed of shaped bodies.

The restriction of the amount of liquid peptizing auxiliary used with which the shaped catalyst bodies are impregnated brings about a maximum increase in the mechanical strength. If the shaped catalyst bodies are treated with an excess of the peptizing auxiliary, the quantifiable increase decreases significantly until finally only a very small effect can be observed, which will he shown in the examples and comparative examples described below. Compared to the finished shaped catalyst bodies used in the present process, increases in the mechanical strength by up to a factor of 3.0 can be achieved. The cutting hardness and/or lateral compressive strength, with which a person skilled in the art will be familiar, can serve as measure of the mechanical strength, Customary measurement methods for this purpose are explained below in connection with the examples.

The mechanism which leads to the increase in the mechanical strength of shaped catalyst bodies according to the present invention has not yet been explained with ultimate certainty. However, it is presumed that the impregnation with the peptizing auxiliary and the subsequent thermal treatment creates new OH groups on the surfaces of the shaped catalyst bodies. These fresh OH groups form new networks in the shaped catalyst bodies during calcination according to the present invention, and these new networks in turn increase the mechanical strength but do not have an effect on the available pore volume.

Measurements of the pore volume have shown that the pore volume changes only very insignificantly (within normal measurement accuracy) and even tends to increase, as shown in the examples below.

As will also he shown below with the aid of examples and comparative examples, the process of the invention does not at all impair the chemical performance of the shaped catalyst bodies. In addition, the process of the invention can be applied to many different catalyst materials, as the examples below likewise demonstrate.

The present invention will be described in more detail in the following.

For the purposes of the present invention, "finished shaped catalyst bodies" are shaped bodies which have been produced by processes known to those skilled in the art and are used in this form as shaped catalyst bodies according to the prior art. The conventional production process quite generally comprises provision of the starting materials and optionally auxiliaries and mixing to form a raw composition, shaping of the raw composition and one or more thermal treatments to separate off volatile materials and to strengthen the shaped bodies (e.g. calcination).

The term shaped body comprises both the catalyst support material and the catalytically active component. The catalytically active component can optionally form all of the shaped body, i.e. the corresponding catalyst does not comprise any additional support material.

The peptizing auxiliaries for impregnating the shaped catalyst bodies in process step b) can be present in solid or liquid form. Solid peptizing auxiliaries are dissolved in a suitable solvent and then used for impregnating the shaped bodies, while liquid peptizing auxiliaries can be used undiluted or likewise as solution. As suitable peptizing auxiliaries for the purposes of the present invention, preference is given to bases such as ammonia or acids such as nitric acid, formic acid or acetic acid, in particular in aqueous, i.e. diluted, form.

Preference is given to using an ammonia solution or a nitric acid solution, in particular an aqueous ammonia solution or an aqueous nitric acid solution, as peptizing auxiliary. Very particular preference is given to using an aqueous ammonia solution. In the case of increasing the strength of shaped zeolite bodies, in particular shaped boron-beta-zeolite bodies, an aqueous ammonia solution displays the best effects.

On the other hand, an aqueous nitric acid solution, for example, has a better effect in increasing the strength of shaped bodies composed of $NiO/CoO/CuO/ZrO_2$.

The upper limit (maximum value) of the theoretical water absorption of the respective shaped catalyst body must not be exceeded, or be exceeded only insignificantly, by the impregnation with the respective amount of liquid peptizing auxiliary for the purposes of the present invention. For the purposes of the present invention, exceeded only insignificantly means exceeded by not more than 5% of the upper limit (maximum value) of the theoretical water absorption. However, for the purposes of the present invention, the amount of liquid peptizing auxiliary used should be at least 50% (minimum amount of peptizing auxiliary) based on the upper limit (maximum value) of the theoretical water absorption of the respective shaped catalyst body, preferably at least 90% of the upper limit. For the purposes of the present invention, the amount of liquid peptizing auxiliary used in step b) is particularly preferably that which corresponds exactly to the theoretical water absorption of the respective shaped catalyst body (i.e. the upper limit).

To form a sufficient number of new active groups on the surface of the shaped catalyst bodies, preference is given to carrying out the process step bb) of allowing the peptizing auxiliary to act for up to 10 hours after process step b). Although a time of allowing to not of from 1 to 10 hours is preferred, the allowing to act can also be carried out for only a few minutes, for example from 1 to 30 minutes, or up to 1 hour, in each case depending on the type and structure of the shaped catalyst bodies.

For very quantitative removal of the peptizing auxiliary with which the shaped bodies have been impregnated in step b), it has been found to he advantageous for the thermal treatment in process step c) he carried out under atmospheric pressure or under reduced pressure, preferably at from 0.1 to 0.9 bar, and/or in a static or agitated bed of the shaped catalyst bodies.

The thermal treatment in process step c) is preferably carried out at from 50° C. to 250° C., in particular from 100° C. to 200° C., and serves to remove the peptizing auxiliary from the shaped catalyst bodies again after impregnation.

In contrast, the calcination in process step d) preferably takes place at from 250° C. to 600° C., in particular from 300° C. to 500° C. The calcination builds up the network of the shaped catalyst bodies again and thus increases the mechanical strength. In determining the calcination temperatures to be employed, account has to be taken of the thermal stability of the catalyst materials used, both support and active component.

It is likewise desirable to carry out the calcination in process step d) in a static or agitated bed of the shaped catalyst bodies in order to achieve a uniform calcination result.

If the shaped catalyst body also comprises a support material, it is in principle possible to use all support materials known to those skilled in the art. The support material is preferably selected from among $SiO_2$, $TiO_2$, $Al_2O_3$ and $ZrO_2$. As catalytically active component, it is in principle possible to use all catalytically active components known to those skilled in the art, for example noble metals such as platinum, palladium, silver, rhodium or base metals such as nickel, cobalt, copper, ruthenium, iron or combinations thereof, and in addition various doping elements which can optionally he present in elemental or oxidic form.

Preference is given to using extrudates and/or pellets and/or granules as shaped catalyst bodies.

Furthermore, preference is given to using heterogeneous catalysts as catalyst for he shaped catalyst bodies.

In practice, it has been found to be advantageous for many fields of use for the catalyst to be selected from among zeolite, in particular boron-beta-zeolite, $NiO/CoO/CuO/ZrO_2$, $TiO_2$, $CuO/Al_2O_3$ and $Co_3O_4/SiO_2$.

The abovementioned object is achieved, in a second aspect of the invention, by shaped catalyst bodies which can be produced by the above-described process of the invention. This ensures that the mechanical strength of the shaped catalyst bodies is improved in a simple but effective way.

In particular, these shaped catalyst bodies have a cutting hardness and/or lateral compressed strength which is higher by a factor of from 1.4 to 3.0 compared to the finished shaped catalyst bodies used. Customary measurement methods for this purpose are explained below in connection with the examples.

The cutting hardness and the lateral compressive strength of shaped catalyst bodies are a measure of the mechanical strength thereof. For industrial uses in known catalyzed reactions, for example reactions catalyzed by zeolites, a cutting hardness of >10 N. preferably >20 N. or a lateral compressive strength of >10 N. preferably >20 N. is desirable. Higher cutting hardnesses or lateral compressive strengths tend to be preferred since many shaped catalyst bodies which were originally sufficiently mechanically strong become soft under reaction conditions.

The catalyst is preferably a boron-beta-zeolite and the shaped catalyst bodies preferably have an average cutting hardness of at least 105 N. This makes it far superior in terms of mechanical strength over conventional boron-beta-zeolites.

The shaped catalyst bodies of the invention can preferably be used for preparing amines or in fixed-bed reactors or fluidized-bed reactors.

A further aspect of the present invention relates to a chemical synthesis process in the presence of shaped catalyst bodies of the invention. The synthesis is, in particular, the preparation of amines by reaction of ammonia or primary or secondary amines with olefins at elevated temperatures and pressures. As an alternative, the synthesis can be a reaction of unsaturated hydrocarbons, alcohols, carbonyl compounds, nitro compounds or nitriles with hydrogen and/or ammonia. The unsaturated hydrocarbons are in particular alkenes (olefins) and alkynes.

Further features, advantages and possible uses can be derived from the following description of preferred examples which do not, however, restrict the invention, Here, all features described form, either in themselves or in any combination, the subject matter of the invention, regardless of whether they are summarized in the claims or the back-references thereof.

The measurement of the cutting hardness was carried out using an instrument from Zwick-Roell, model BZ 2.5/TS1S, with fixed support plate and a freely movable, vertical blade holder whose blade presses the shaped body against the fixed plate (initial force 0.5 N, initial force speed 10 mm/min, sinking speed 3 mm/min). The freely movable blade holder is connected to a load cell for recording the force, The instrument is controlled by means of a computer which records and evaluates the measured values. Extrudates of the shaped bodies having a predetermined diameter are loaded with a blade (thickness 0.6 mm, flat) under increasing force until fracture of the extrudates occurs. The force at fracture is referred to as the cutting hardness. The measured value reported is the mean from testing of 30 shaped bodies, This method is also described in DE 103 26 137 A1, EP 1 996 543 B1 and WO 2011/048128 A2.

The measurement of the lateral compressive strength was carried out using a testing instrument from Zwick, Ulm, having a fixed rotatable plate and a freely movable, vertical punch which presses the shaped bodies (in the form of pellets, rings or spheres) against the fixed rotatable plate. The shaped bodies are as a result loaded with increasing force on the cylindrical surface between the two parallel plates until fracture occurs. The force registered on fracture is the lateral compressive strength. The freely movable punch was connected to a load cell for recording the force. The instrument was controlled by a computer which recorded and evaluated the measured values. 25 defect-free (i.e. crack-free and without broken edges) shaped bodies in pellet form were taken from a number of specimens, and the lateral compressive strength of these was determined and subsequently averaged. This method is also described in DE 199 42 300 A1 and EP 1 431 273 A1.

EXAMPLE 1

Shaped Boron-beta-zeolite Body, Hardening by Means of Aqueous Ammonia Solution

A shaped boron-beta-zeolite body extruded with aluminum oxide is produced as described in example 1 of WO 2010/121974 A2. The average cutting hardness is 37 N and the shaped body has a pore volume determined by mercury porosimetry of 0.42 ml/g (catalyst 1a). This catalyst produced in this way is then impregnated on a Rotavapor (trade name of Büchi) with a 10% strength aqueous ammonia solution to the theoretical water absorption (maximum value) and allowed to stand for 2 hours at room temperature. The catalyst is then dried at 150° C. under reduced pressure and with rotation. The catalyst which has been dried in this way is subsequently transferred to a rotary flask and calcined at 450° C. for 2 hours with rotation. The average cutting hardness of the resulting catalyst (catalyst 1b) is found to be 105 N, which corresponds to an increase by a factor of 2.83. The catalyst has a pore volume determined by mercury porosimetry of 0.43 ml/g.

Shaped boron-beta-zeolite bodies are suitable, in particular, for the synthesis of amines, in particular t-butylamine (tBA).

10 g of each of the catalysts 1a and 1b produced in this way are, after comminution to give crushed catalyst material, installed in a tube reactor (6 mm internal diameter) and supplied under isothermal conditions at 270° C. and a pressure of 270 bar with 43 g/h of a mixture of isobutene and $NH_3$ (1 mol:1.5 mol) and the reaction is monitored by means of on-line gas chromatography. A yield of 13.8-14.3 g of tBA/g of feed at a selectivity of at least 99% is achieved both when using catalyst 1a and when using catalyst 1b.

COMPARATIVE EXAMPLE 1

Shaped Boron-beta-zeolite Body, Hardening with Aqueous Ammonia Solution

A shaped B-beta-zeolite body extruded with aluminum oxide is produced as described in example 1 of WO 2010/121974 A2. The average cutting hardness is 37 N (catalyst 1a). This catalyst produced in this way is then impregnated in a Rotavapor with an excess of a 10% strength aqueous ammonia solution which corresponds to twice the theoretical water absorption of the shaped bodies (twice the maximum value), and the mixture is allowed to stand at room temperature for 2 hours. The catalyst is then dried at 150° C. under reduced pressure and with rotation. The catalyst which has been dried in this way is subsequently transferred to a rotary flask and calcined at 450° C. for 2 hours with rotation. The average cutting hardness of the resulting catalyst is found to be 47 N, which corresponds to an increase by a factor of 1.27.

EXAMPLE 2

Shaped $NiO/CoO/CuO/ZrO_2$ Body, Hardening with Aqueous Ammonia Solution

A precipitation of a metal salt solution comprising 29.4 kg of nickel nitrate solution (17.4% NiO content), 8.8 kg of copper nitrate solution (19.3% CuO content) and 16.3 kg of zirconium acetate solution (18.7% $ZrO_2$ content) with a 20% strength sodium carbonate solution is carried out at a pH of 5.7 and a temperature of 70° C. After the metal salt solution has been consumed, the pH is set to 7.4 by means of a sodium carbonate solution. After stirring for 12 hours and cooling to room temperature, the suspension obtained is filtered and the filter cake is washed with distilled water until a sodium content in the filter cake (after heat treatment at 900° C.) of <0.1% is attained. The washed filter cake is dried at 120° C. for 12 hours and subsequently calcined at 480° C. for 3 hours. The powder obtained in this way is mixed with 3% of graphite and pressed on a tableting press to form 6×3 mm pellets. The average lateral compressive strength of this catalyst 2a) is 105 N.

This catalyst produced in this way is then impregnated with a 10% strength aqueous ammonia solution to the theoretical water absorption and allowed to stand at room temperature for 2 hours. The catalyst is then dried at 150° C. under reduced pressure. The catalyst which has been dried in this way is subsequently calcined at 450° C. for 2 hours. The average lateral compressive strength of the resulting catalyst 2b) is found to be 260 N, which corresponds to an increase by a factor of 2.47. The catalyst has a pore volume determined by mercury porosimetry of 0.19 ml/g.

Shaped $NiO/CoO/CuO/ZrO_2$ bodies can be used, in particular, in hydrogenation or amination reactions.

COMPARATIVE EXAMPLE 2

Shaped $NiO/CoO/CuO/ZrO_2$ Bodies, Hardening with Aqueous Ammonia Solution

A precipitation of a metal salt solution comprising 29.4 kg of nickel nitrate solution (17.4% NiO content), 8.8 kg of copper nitrate solution (19.3% CuO content) and 16.3 kg of zirconium acetate solution (18.7% $ZrO_2$ content) with a 20% strength sodium carbonate solution is carried out at a pH of 5.7 and a temperature of 70° C. After the metal salt solution has been consumed, the pH is set to 7.4 by means of a sodium carbonate solution. After stirring for 12 hours and cooling to room temperature, the suspension obtained is filtered and the filter cake is washed with distilled water until a sodium content in the filter cake (after heat treatment at 900° C.) of <0.1% is attained. The washed filter cake is dried at 120° C. for 12 hours and subsequently calcined at 480° C. for 3 hours. The powder obtained in this way is mixed with 3% of graphite and pressed on a tableting press to form 6×3 mm pellets. The average lateral compressive strength of this catalyst 2a) is 105 N and the shaped body has a pore volume determined by mercury porosimetry 0.18 ml/g.

This catalyst produced in this way is then impregnated with a 10% strength aqueous ammonia solution corresponding to twice the theoretical water absorption of the shaped bodies and the mixture is allowed to stand at room temperature for two hours. The catalyst is then dried at 150° C. under reduced pressure. The catalyst which has been dried in this way is subsequently calcined at 450° C. for 2 hours. The average lateral compressive strength of the resulting catalyst 2b) is found to he 116 N, which corresponds to an increase by a factor of 1.10.

EXAMPLE 3

Shaped $NiO/CoO/CuO/ZrO_2$ Bodies, Hardening with Dilute Nitric Acid

Catalyst 2a) is impregnated with a 5% strength aqueous nitric acid solution to the theoretical water absorption and allowed to stand at room temperature for 2 hours. The catalyst is then dried at 150° C. under reduced pressure. The catalyst which has been dried in this way is subsequently calcined at 450° C. for 2 hours. The average lateral compressive strength of the resulting catalyst 3) is found to he 300 N, which corresponds to an increase by a factor of 2.85. The catalyst has a pore volume determined by mercury porosimetry of 0.21 ml/g.

EXAMPLE 4

Shaped $TiO_2$ Body, Hardening with Dilute Nitric Acid 7.8 kg of $TiO_2$ (S150 from Finnti, 86% pure) are processed with 33 g of Tylose. (Clariant H4000 G4), 65 g of stearic acid and also 250 g of 3% strength nitric acid and 24 kg of water in a pan mill to form an extrudable composition and molded in an extruder to give 1.5 mm extrudates. The extrudates obtained are dried at 120° C. for 12 hours and subsequently calcined at 400° C. The average cutting hardness of this catalyst is 11 N and the shaped body has a pore volume determined by mercury porosimetry of 0.32 ml/g.

This catalyst produced in this way is then impregnated with a 5% strength aqueous nitric acid solution to the theoretical water absorption and allowed to stand at room temperature for 2 hours, The catalyst is then dried at 150° C. under reduced pressure. The catalyst which has been dried in this way is subsequently calcined at 400° C. for 2 hours. The average cutting hardness of the resulting catalyst 4) is found to be 20 N. which corresponds to an increase by a factor of 1.81. The catalyst has a pore volume determined by mercury porosimetry of 0.35 ml/g.

Shaped $TiO_2$ bodies can be used, in particular, in C—N, C—O, C—C coupling reactions.

EXAMPLE 5

Shaped $CuO/Al_2O_3$ Bodies, Hardening with Dilute Nitric Acid

A precipitation of a metal salt solution comprising 7.1 kg of copper nitrate solution (19.3% CuO content) and 13.8 kg of aluminum nitrate solution (8.1% $Al_2O_3$ content) with a 20% strength sodium carbonate solution is carried out at a pH of 5.8 and a temperature of 80° C. After consumption of the metal salt solution, the pH is set to 8.1 by means of a sodium carbonate solution. After stirring for 12 hours and cooling to room temperature, the suspension obtained is filtered and the filter cake is washed with distilled water until a sodium content in the filter cake (after heat treatment at 900° C.) of <1% is attained. The washed filter cake is dried at 120° C. for 12 hours and subsequently calcined at 350° C. for 3 hours. The powder obtained in this way is mixed with 3% of graphite and pressed on a tableting press to form 3×3 mm pellets. The average lateral compressive strength of this catalyst 2a) is 56 N and the shaped body has a pore volume determined by mercury porosimetry of 0.41 ml/g.

This catalyst produced in this way is then impregnated with a 5% strength aqueous nitric acid solution to the theoretical water absorption and allowed to stand at room temperature for two hours. The catalyst is then dried at 150° C. under reduced pressure. The catalyst which has been dried in this way is subsequently transferred to a rotary flask and calcined at 450° C. for 2 hours. The average lateral compressive strength of the resulting catalyst 5) is found to be 81 N. which corresponds to an increase by a factor of 1.44. The catalyst has a pore volume determined by mercury porosimetry of 0.46 ml/g.

Shaped $CuO/Al_2O_3$ bodies can be used, in particular, in hydrogenation reactions.

EXAMPLE 6

Shaped $Co_3O_4/SiO_2$ Body, Hardening with Dilute Nitric Acid

A precipitation of a metal salt solution comprising 14.7 kg of cobalt nitrate solution (17.1% $Co_3O_4$ content) with a 20% strength sodium carbonate solution is carried out at a pH of 7.0 and a temperature of 70° C. After stirring for 12 hours and cooling to room temperature, the suspension obtained is filtered and the filter cake is washed with distilled water until a sodium content in the filter cake (after heat treatment at 900° C.) of <3% is attained. The washed filter cake is dried at 120° C. for 12 hours and subsequently calcined at 500° C. for 3 hours. 2 kg of this powder obtained in this way are processed with 0.69 kg of Silres MSE 100, 26.9 g of Walocel, 270 g of 56% strength nitric acid and also 250 g of water in a kneader to give an extrudable composition and molded by means of an extruder to form 4 mm extrudates. The extrudates obtained are dried at 120° C. for 12 hours and subsequently calcined at 570° C. The average cutting hardness of this catalyst is 59 N.

This catalyst produced in this way is then impregnated with a 5% strength aqueous nitric acid solution to the theoretical water absorption and allowed to stand at room temperature for 2 hours. The catalyst is then dried at 150° C. under reduced pressure. The catalyst which has been dried in this way is subsequently calcined at 400° C. for 2 hours. The average cutting hardness of the resulting catalyst 6) is found to be 90 N, which corresponds to an increase by a factor of 1.52.

Shaped $Co_3O_4/SiO_2$ bodies can, in particular, be used in hydrogenation reactions.

Evaluation

Example 1) makes it clear that the process of the invention leads to a significantly increased mechanical strength of the shaped catalyst bodies. At the same time, it is demonstrated by the synthesis of t-butylamine in a comparative experiment that the increase in the mechanical strength can be brought about without the chemical performance of the catalyst being impaired.

Comparative example 1) shows that the impregnation with the peptizing auxiliary can be carried out advantageously only to the maximum value of the theoretical water absorption since excess amounts of liquid lead only to a very small hardening effect.

Examples 3) to 6) demonstrate that the process of the invention can also be applied successfully to various other catalyst systems.

The invention claimed is:

1. A process for treating shaped catalyst bodies, which comprises the process steps:
    a) providing finished shaped catalyst bodies,
    b) impregnating the finished shaped catalyst bodies with a peptizing auxiliary in an amount of liquid which does not exceed the theoretical water absorption of the shaped catalyst bodies,
    c) thermal treating the impregnated shaped catalyst bodies at from 50° C. to 250° C. and
    d) calcinating the thermally treated shaped catalyst bodies at from 250° C. to 600° C.

2. The process according to claim 1, wherein an ammonia solution or a nitric acid solution is used as peptizing auxiliary.

3. The process according to claim 2, wherein an aqueous ammonia solution or an aqueous nitric acid solution is used as peptizing auxiliary.

4. The process according to claim 1, which, after process step b), further comprises the process step
    bb) allowing the peptizing auxiliary to act for up to 10 hours.

5. The process according to claim 1, wherein the thermal treatment in process step c) is carried out under atmospheric pressure or under reduced pressure or in a static or agitated bed of the shaped catalyst bodies.

6. The process according to claim 5, wherein the reduced pressure is from 0.1 to 0.9 bar.

7. The process according to claim 1, wherein the calcination in process step
    d) is carried out in a static or agitated bed of the shaped catalyst bodies.

8. The process according to claim 1, wherein extrudates or pellets or granules are used as shaped catalyst bodies.

9. The process according to claim 1, wherein heterogeneous catalysts are used as catalyst for the shaped catalyst bodies.

10. The process according to claim 1, wherein the catalyst is zeolite, $NiO/CoO/CuO/ZrO_2$, $TiO_2$, $CuO/Al_2O_3$ or $Co_3O_4/SiO_2$.

11. The process according to claim 10, wherein the zeolite is a boron-beta-zeolite.

12. A shaped catalyst body which has increased mechanical strength and can be produced by the process according to claim 1.

13. The shaped catalyst body according to claim 12, wherein the shaped catalyst body has a cutting hardness or lateral compressive strength which is higher by a factor of from 1.4 to 3.0 than that of the finished shaped catalyst body used.

14. The shaped catalyst body according to claim 12, wherein the catalyst is a boron-beta-zeolite and the shaped catalyst body has an average cutting hardness of at least 105 N.

15. A process for the preparation of amines which comprises reacting ammonia, a primary amine or a secondary amine with an olefin at elevated temperature and pressure in the presence of the shaped catalyst body according to claim 12.

16. A process for operating fixed-bed reactors which comprises the steps
    providing the shaped catalyst body according to claim 12 as a fixed-bed,
    introducing one or more educts to the fixed bed reactors at elevated temperature or pressure
    and
    carrying out a chemical synthesis process.

17. A chemical synthesis process in the presence of the shaped catalyst bodies according to claim 12 which comprises reacting unsaturated hydrocarbons, alcohols, carbonyl compounds, nitro compounds or nitriles with hydrogen or ammonia.

18. The chemical synthesis process according to claim 17, wherein the synthesis is the preparation of amines by reaction of ammonia or primary or secondary amines with olefins at elevated temperatures and pressures.

19. The chemical synthesis process according to claim 17, wherein the synthesis is a reaction of unsaturated hydrocarbons, alcohols, carbonyl compounds, nitro compounds or nitriles with hydrogen or ammonia.

20. A process for operating fluidized bed reactors which comprises the steps providing the shaped catalyst body according to claim 12 in a fluidized bed reactor, fluidizing the shaped catalyst bodies according to claim 12 to become a fluidized bed, introducing one or more educts to the fluidized bed reactor at elevated temperature or pressure and
 carrying out a chemical synthesis process.

\* \* \* \* \*